(12) United States Patent
Cattin-Liebl

(10) Patent No.: US 7,959,289 B2
(45) Date of Patent: Jun. 14, 2011

(54) OPHTHALMOLOGICAL DEVICE AND OPHTHALMOLOGICAL MEASURING METHOD

(75) Inventor: Roger Cattin-Liebl, Grenchen (CH)

(73) Assignee: SIS AG, Surgical Instrument Systems (CH)

( * ) Notice: Subject to any disclaimer, the term of this patent is extended or adjusted under 35 U.S.C. 154(b) by 134 days.

(21) Appl. No.: 12/282,575

(22) PCT Filed: Mar. 16, 2006

(86) PCT No.: PCT/CH2006/000153
§ 371 (c)(1),
(2), (4) Date: Mar. 4, 2009

(87) PCT Pub. No.: WO2007/104166
PCT Pub. Date: Sep. 20, 2007

(65) Prior Publication Data
US 2009/0303437 A1    Dec. 10, 2009

(51) Int. Cl.
*A61B 3/14* (2006.01)
*A61B 3/10* (2006.01)
(52) U.S. Cl. .................... 351/206; 351/210; 351/221
(58) Field of Classification Search .......... 351/205–206, 351/210–211, 221, 246
See application file for complete search history.

(56) References Cited

U.S. PATENT DOCUMENTS

| 5,094,521 A * | 3/1992 | Jolson et al. ............. 351/210 |
| 7,264,355 B2 | 9/2007 | Rathjen |
| 2004/0119943 A1 * | 6/2004 | Rathjen ............. 351/211 |
| 2005/0270486 A1 * | 12/2005 | Teiwes et al. ............. 351/209 |

FOREIGN PATENT DOCUMENTS

EP    1 430 829 A1    6/2004

OTHER PUBLICATIONS

International Search Report dated Dec. 1, 2006, issued in corresponding international application No. PCT/CH2006/000153.

* cited by examiner

*Primary Examiner* — Dawayne A Pinkney
(74) *Attorney, Agent, or Firm* — Ostrolenk Faber LLP

(57) ABSTRACT

An opthalmologic device and an opthalmologic measuring method in accordance with an embodiment of the present application in which, cross-sectional images of cross-sectional portions illuminated from different instrument positions by a light projector are captured in Scheimpflug configuration. Furthermore, corresponding top view images are also captured from the different instrument positions. At least one reference section and at least one comparative section are extracted from an initial instrument position or from an advanced instrument position, respectively. The displacement between the reference section and the comparative section is determined and the cross-sectional images are positioned relative to one another, based on the displacement. A coherent examination of the entire eye is made possible in which the relative movements of the eye with respect to the device, particularly rotational movements, are taken into consideration.

28 Claims, 5 Drawing Sheets

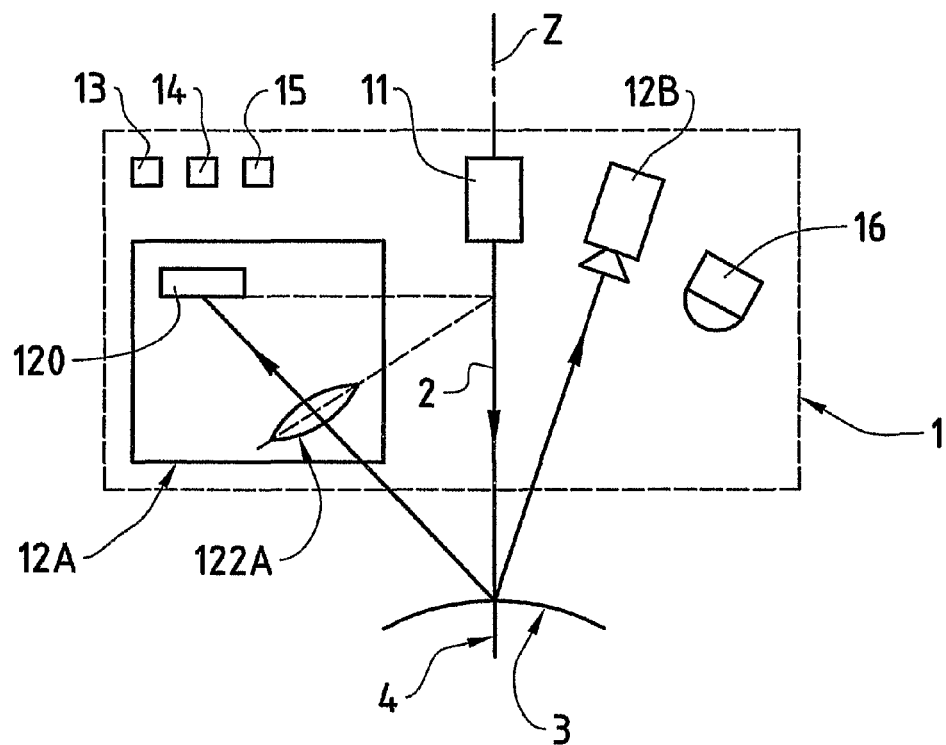
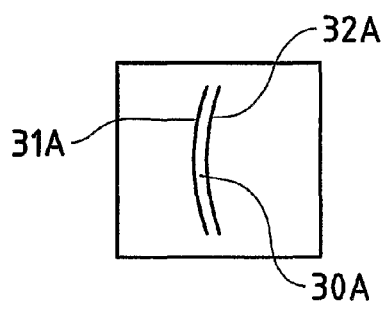
Fig. 2a
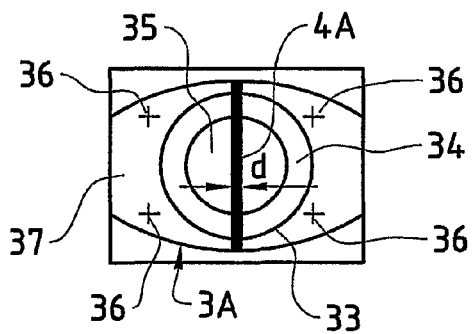
Fig. 2b

OPHTHALMOLOGICAL DEVICE AND OPHTHALMOLOGICAL MEASURING METHOD

CROSS REFERENCE TO RELATED APPLICATIONS

The present application is a 35 U.S.C. §§371 national phase conversion of PCT/CH2006/000153, filed Mar. 16, 2006. The PCT International Application was published in the English language.

FIELD OF THE INVENTION

The present invention relates to an opthalmological device and an opthalmological measuring method. Specifically, the present invention relates to an opthalmological device and an opthalmological measuring method having a light projector projecting a beam of rays through a cross-sectional portion of an eye, image-capturing means disposed in Scheimpflug configuration with respect to the beam of rays and capturing in a first instrument position a cross-sectional image of at least a sub-area of the cross-sectional portion, and a motion driver moving the first image-capturing means to a second instrument position, at which second instrument position the first image-capturing means are disposed in Scheimpflug configuration with respect to the beam of rays.

BACKGROUND OF THE INVENTION

Described in the patent publication U.S. Pat. No. 5,404,884 are a method and a device for examining corneal tissue of a patient. According to U.S. Pat. No. 5,404,884, a substantially planer laser beam with a slit-like profile is directed through a cross-sectional portion of the cornea. By capturing at least a portion of the light scattered in the cornea, a cross-sectional image of the cornea is obtained. From a multiplicity of such cross-sectional images of the cornea, corneal haze, corneal thickness and corneal topography can be determined comprehensively for the whole cornea. Since the eyes can move relative to the examination device, examination of the entire eye as set forth in U.S. Pat. No. 5,404,884 can lead to inaccuracies, however, because these relative movements are not registered and taken into account. With comprehensive examination of the eye based on the merging of a multiplicity of cross-sectional images, measurement artifacts can result as a consequence of the difficulty of mutual alignment of the individual cross-sectional images.

Patent application EP 1430829 describes an opthalmological device and an opthalmological measuring method in which, by means of a light projector, a beam of rays, for example a light slit, is projected through a cross-sectional portion of an eye, in particular through a cross-sectional portion of the cornea of the eye. A cross-sectional image of at least one sub-area of the cross-sectional portion illuminated by the light projector is captured by image-capturing means, which are disposed in Scheimpflug configuration with respect to the beam of rays. Furthermore, a top view image of the eye, comprising an image of the cross-sectional portion illuminated by the first light projector, is captured by further image-capturing means and is stored assigned to the captured cross-sectional image. For a coherent examination of the entire eye, stored cross-sectional images are positioned relative to each other, on the basis of the assigned top view image. Particularly, the relative positioning of the cross-sectional images is determined on the basis of the image of the illuminated cross-sectional portion included in the top view image, and/or on the basis of light markers and/or visible patterns (e.g. a Placido pattern) reflected on the eye and captured in the top view image. Although the opthalmological device and opthalmological measuring method according to EP 1430829 make possible a coherent examination of the entire eye, taking into consideration the relative movements of the eye with respect to the device, rotations of a spherical cornea are not detected properly in the special case where the cornea rotates around its center.

SUMMARY OF THE INVENTION

It is an object of the present invention to propose a new opthalmologic device and a new opthalmologic measuring method which do not have the drawbacks of the state of the art, and which in particular make possible a coherent examination of the entire eye, in particular determination of topography and measurement values for structures of the anterior chamber of the eye, for example the corneal topography and corneal thickness, taking into account relative movements of the eye with respect to the device and rotations of the eye.

According to the present invention, these objects are achieved particularly through the features of the independent claims. In addition, further advantageous embodiments follow from the dependent claims and the description.

The opthalmological device comprises a light projector configured to project a beam of rays through a cross-sectional portion of an eye; first image-capturing means disposed in Scheimpflug configuration with respect to the beam of rays and configured to capture in a first instrument position a cross-sectional image of at least a sub-area of the cross-sectional portion, illuminated by the light projector; a motion driver configured to move the first image-capturing means and the light projector to a second instrument position, at which second instrument position the first image-capturing means are disposed in Scheimpflug configuration with respect to the beam of rays; and second image-capturing means configured to capture a first top view image of at least part of the eye, while capturing the cross-sectional image in the first instrument position, and a second top view image of at least part of the eye, while capturing the cross-sectional image in the second instrument position.

According to the present invention, the above-mentioned objects are particularly achieved in that, the opthalmological device further comprises an extraction module configured to extract at least one reference section from the first top view image, and at least one comparative section from the second top view image; a measurement module configured to determine a displacement between the reference section and the comparative section; and a positioning module configured to position relative to each other cross-sectional images, captured in the first instrument position and the second instrument position, based on the displacement.

Preferably, the reference and comparative sections are each extracted as an array having equal number of rows and columns. Computing the displacement between extracted reference and comparative sections make it possible to take into consideration relative movements of the eye with respect to the device, particularly rotational movements, while examining coherently the entire eye.

In an embodiment, the extraction module is configured to extract the at least one reference section from a natural feature of the eye, preferably an iris structure in the first top view image, and to extract the at least one comparative section from the natural feature of the eye, e.g. the iris structure, in the second top view image. Preferably, the extraction module is configured to extract the reference and comparative sections from an iris structure that is essentially irremovable relative to the eye's eyeball. For example, the extraction module is configured to extract the reference and comparative sections from an iris structure that is essentially adjacent to the eye's limbus.

In an embodiment, the measurement module is further configured to determine cyclotorsion and/or cyclorotation of the eye from a combination of a first set of sections, comprising at least a first reference section and a corresponding first comparative section, and a second set of sections, comprising at least a second reference section and a corresponding second comparative section.

In a further embodiment, the second image-capturing means are further configured to capture with the first and second top view images reflections on the eye. The measurement module is further configured to determine cyclotorsion or cyclorotation of the eye from the displacement between the reference section and the comparative section, and from a displacement determined between reflections in the first top view image and reflections in the second top view image.

Preferably, the second image-capturing means are coupled with the motion driver such that the first top view image is captured from a position linked with the first instrument position, and the second top view image is captured from a position linked with the second instrument position. Furthermore, the device comprises a compensator module configured to determine the at least one comparative section from the second top view image, using a reverse transformation to compensate for movement of the second image-capturing means.

Preferably, the measurement module is configured to determine the displacement using a phase-correlation algorithm. For example, the measurement module is configured to determine the displacement using sub-pixel phase-correlation.

In an embodiment, the extraction module is configured to extract the reference section with an area larger than the area of the comparative section. The measurement module is configured to determine an initial displacement value using a phase-correlation algorithm for the comparative section and for a partial reference section having a defined location within the reference section, and to determine the displacement using sub-pixel phase-correlation for the partial reference section being moved off the defined location by the initial displacement value. For example, the defined location of the partial reference section is determined from previous displacement measures or the center of the reference section is taken as the defined location.

In different embodiments, the motion driver is configured to rotate the light projector and the first image-capturing means essentially about a normal to the surface of the eye, turned toward the light projector, or to shift them substantially perpendicular to this normal.

BRIEF DESCRIPTION OF THE DRAWINGS

The present invention will be explained in more detail, by way of example, with reference to the drawings in which:

FIG. 1 shows a block diagram illustrating schematically an opthalmological device with a light projector, image-capturing means for capturing a cross-sectional image of an eye as well as a top view image of the eye.

FIG. 2a shows a cross-sectional image of an illuminated cross-sectional portion of an eye (cornea).

FIG. 2b shows a top view image of the eye with an illuminated cross-sectional portion.

DETAILED DESCRIPTION OF THE PREFERRED EMBODIMENTS

Figure 3:
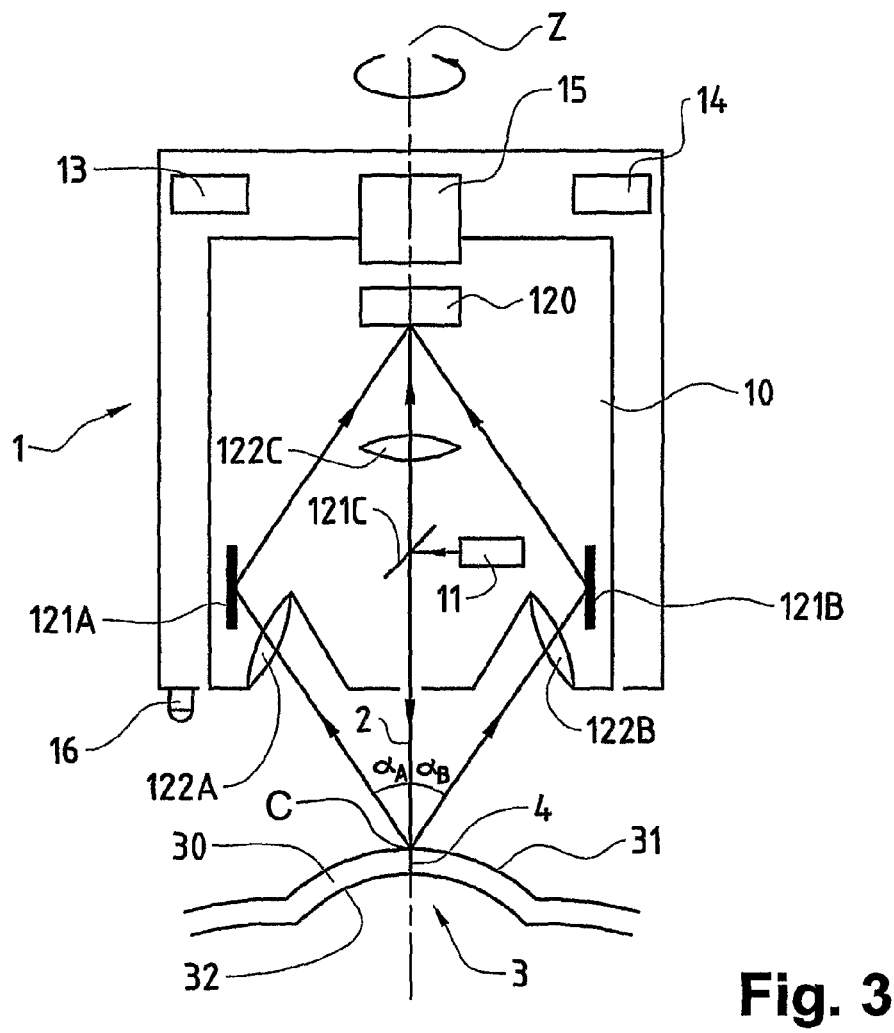
FIG. 3 shows a block diagram illustrating schematically an opthalmological device with a light projector and image-capturing means for capturing two cross-sectional images and a top view image of an eye in which light rays for generating the top view image, and light rays for generating the two cross-sectional images from different positions, are supplied to a common image converter by means of ray-redirecting optical means.

In FIGS. 1 and 3, reference numeral 1 refers to an opthalmological device, different embodiments of the opthalmologic device 1 being explained in the following description with reference to these figures. Otherwise same, corresponding components are designated in the figures by the same reference numerals.

As illustrated in FIGS. 1 and 3, the opthalmological device 1 comprises a light projector 11 for projection of a beam of rays 2 through a cross-sectional portion 4 of an eye 3, in particular through a cross-sectional portion of the cornea 30 of the eye 3. The beam of rays 2 is projected preferably in the form of a light slit. The light projector 11 comprises, for example, a slit lamp or a laser whose light is shaped into a fan through beam transformation optics.

Furthermore, the opthalmological device 1 comprises image-capturing means for capturing and storing a cross-sectional image 30A of at least one sub-area of the cross-sectional portion 4 illuminated by the light projector 11, which means are disposed in Scheimpflug configuration with respect to the beam of rays 2. The opthalmological device 1 comprises moreover further image-capturing means for capturing a top view image 3A of the eye 3, which comprises in an embodiment an image of the illuminated cross-sectional portion 4A (this is not a requirement), and for storing the captured top view image 3A, and the image of the illuminated cross-sectional portion 4A possibly contained therein, assigned to the captured cross-sectional image 30A. Depending on the embodiment, the image-capturing means comprise, image-capturing devices 12A, 12B, for instance CCD cameras (Charged Coupled Device) or CMOS cameras (Complementary Metal-Oxide-Silicon), image converter 120, for example CCD chips or CMOS chips, ray-redirecting optical elements 121A, 121B, for instance mirrors, ray-redirecting optical elements 121C, for example beam-splitting optical elements such as semi-transparent mirrors, and/or imaging optical elements 122A, 122B, 122C, for instance lenses. Shown in FIG. 3 is an embodiment of the opthalmological device 1 in which the beam of rays 2, running through the cross-sectional portion 4, and the optic axis of the image-capturing means for capturing the top view image 3A coincide. The imaging optical elements 122A and the ray-redirecting optical element 121A direct to the image converter 120 the light rays for capturing the cross-sectional image 30A from a first position at an angle of observation $\alpha_A$. The additional imaging optical elements 122B and the additional ray-redirecting optical element 121B likewise direct to the image converter 120 the light rays for capturing the cross-sectional image 30B from a second position at the angle of observation $\alpha_B$. The two positions are preferably located on different sides of the beam of rays 2, and the magnitudes of the observation angles $\alpha_A$ and $\alpha_B$ are preferably equal. Furthermore, the embodiment according to FIG. 3 makes it possible to capture the cross-sectional images 30A, 30B as well as the top view image 3A by means of a single common image converter 120. Through averaging measurements from two cross-sectional images 30A and 30B, captured from different positions, measurement values can be determined more precisely in the opthalmologic device 1 according to FIG. 3. For example, the corneal thickness D can be determined more precisely from the measurement values $D_A$ and $D_B$, as described in the European Patent EP 1358839. Also in the embodiment according to FIG. 3, the top view image 3A can be captured by a separate image-capturing device 12B as shown in FIG. 1. Further possible embodiments of the image-capturing means are described in EP 1430829.

Figure 4:
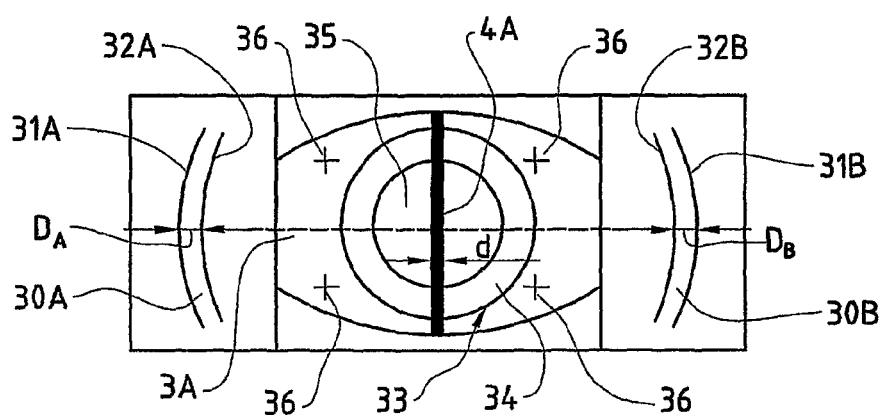
FIG. 4 shows a combined image with two cross-sectional images of an illuminated cross-sectional portion of the eye from two different positions, and a top view image of the eye with the illuminated cross-sectional portion.
Figure 5:
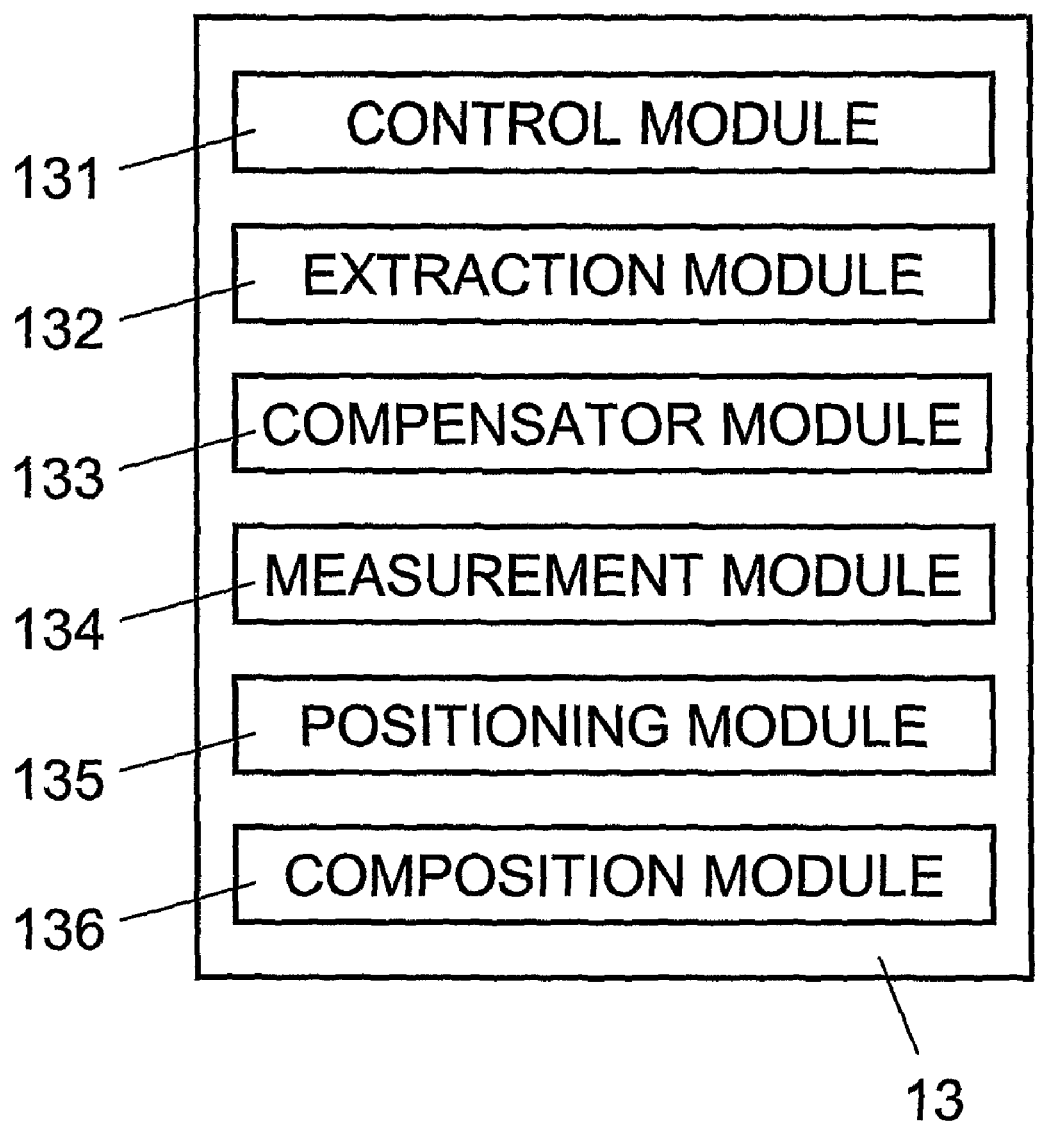
FIG. 5 shows a block diagram illustrating schematically processing means with functional modules for processing captured top view images and cross-sectional images.

Shown in FIG. 2a is a cross-sectional image 30A, captured by the image-capturing means 12A, of the illuminated cross-sectional portion 4 of the eye 3. The top view image 3A of the eye 3 shown in FIG. 2b is captured by image-capturing device 12B. Shown in FIG. 4 is the combined cross-sectional image 30A, top view image 3A and cross-sectional image 30B, captured by the image converter 120 of the embodiment according to FIG. 9. For the sake of simplicity, further structures of the eye 3, such as iris or lens, are not shown in FIGS. 2a and 4. Visible in the cross-sectional images 30A, 30B are in particular a cross-sectional image of the anterior corneal surface 31A, 31B and a cross-sectional image of the posterior corneal surface 32A, 32B. Visible in the top view image 3A are in particular an image of the illuminated cross-sectional portion 4A with the finite thickness d, reflections of projected light markers 36, as well as limbus 33, iris 34 and pupil 35 of the eye 3.

To make natural eye features visible, such as limbus 33, iris 34, pupil 35, pupil edge 38, and/or to produce reflections of artificial light markers 36, the opthalmological device 1 comprises one or more additional light sources 16. In particular to make natural eye features visible, one or more infrared light-emitting diodes can be used, for instance. In an embodiment, the opthalmological device 1 further comprises a screen element provided with a visible pattern, a so-called Placido pattern, which is reflected by the surface of the eye 3. The natural and/or artificial reference features are co-captured in the top view image 3A of the eye 3.

The opthalmological device 1 further comprises a motion driver 15 to rotate the light projector 11 and the image-capturing means substantially about a normal to the surface of the eye 3 turned towards the light projector 11 or to shift these components substantially perpendicular to this normal. As shown schematically in FIG. 3, the light projector 11 and the image-capturing means 120, 121A, 121B, 121C, 122A, 122B, 122C are mounted for this purpose on a movable carrier device 10, which is driven by the motion driver 15. As illustrated in FIG. 1, in different embodiments, the image-capturing means for capturing the top view image 3A of the eye 3, e.g. the image-capturing device 12B, is either linked to and moved by the motion driver 15, or fixed and not coupled to the motion driver 15. The motion driver 15 preferably comprises a rotation driver, for instance an electromotor, which rotates the carrier device 10 about the optic axis Z of the eye.

As is illustrated schematically in FIGS. 1 and 3, the opthalmological device 1 further comprises processing means 13 with functional modules for processing captured top view images 3A and cross-sectional images 30A, 30B, e.g. a control module 131, an extraction module 132, a compensator module 133, measurement module 134, a positioning module 135, and a composition module 136. Furthermore, the processing means 13 comprise at least a processor, data- and program-memory. The functional modules are implemented preferably as software modules, which are stored in the program memory and are executed on the processor. One skilled in the art will understand that the functional modules can also be executed partially or completely through hardware. In the following paragraphs, the functional modules will be described with reference to FIGS. 5, 6, 7 and 8.

Figure 6:
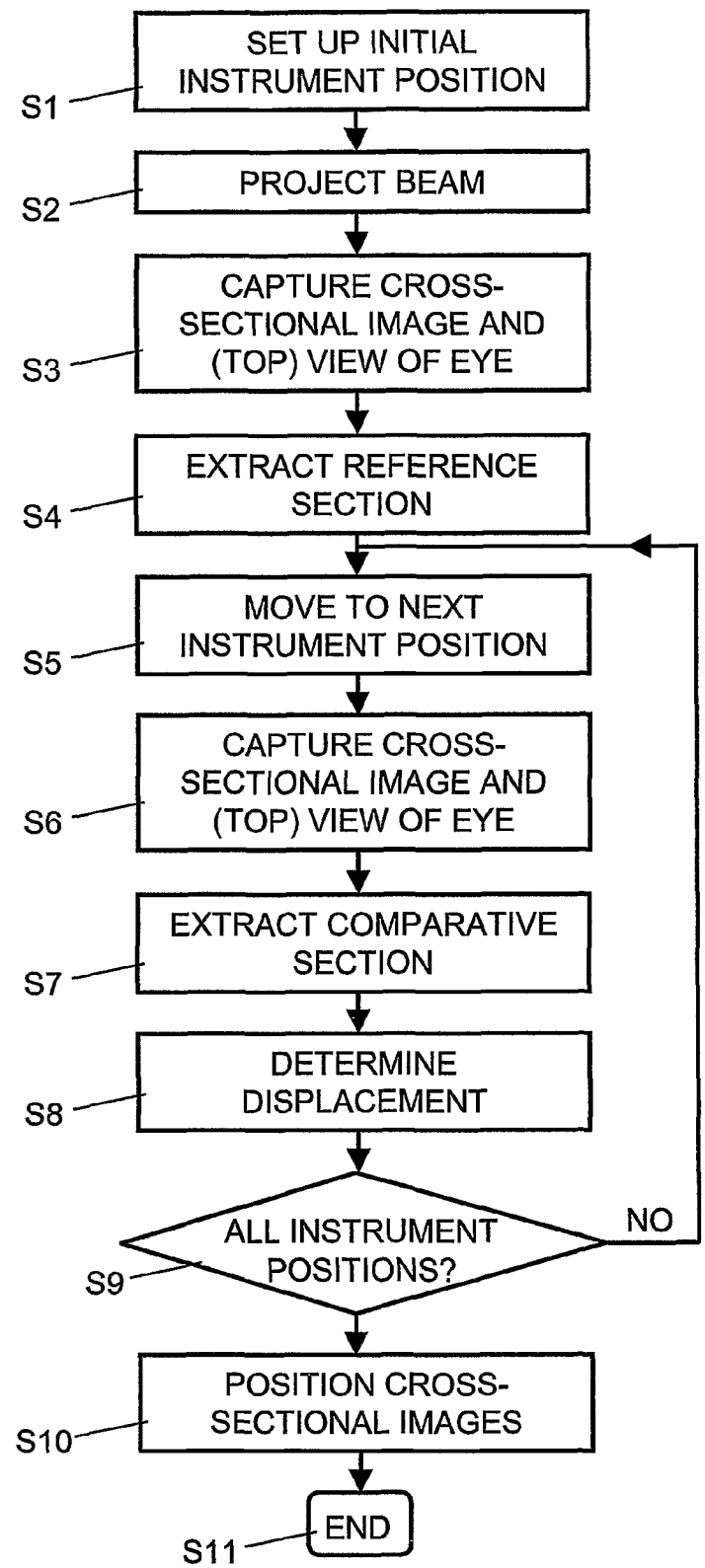
FIG. 6 shows a flow diagram of a possible sequence of steps for relative positioning (mutual alignment) of cross-sectional images of the eye.

As illustrated in FIG. 6, in step S1, the control module 131 makes the motion driver 15 set the opthalmological device 1 in an initial instrument position, i.e. the light projector 11 and the image-capturing means coupled with the motion driver 15 are placed in defined respective positions associated with the initial instrument position.

In step S2, the control module 131 makes the light projector 11 projects the beam of rays 2 through the cross-sectional portion 4 of the eye 3. In different embodiments, the beam of rays 2 is projected continuously or it is interrupted by movements to an advanced instrument position.

In step S3, the control module 131 makes the image-capturing means capture one or two cross-sectional images 30A, 30B as well as a top view image 3A from the initial instrument position. The cross-sectional images 30A, 30B and the top view image 3A from the initial instrument position are stored assigned to each other.

Figure 7:
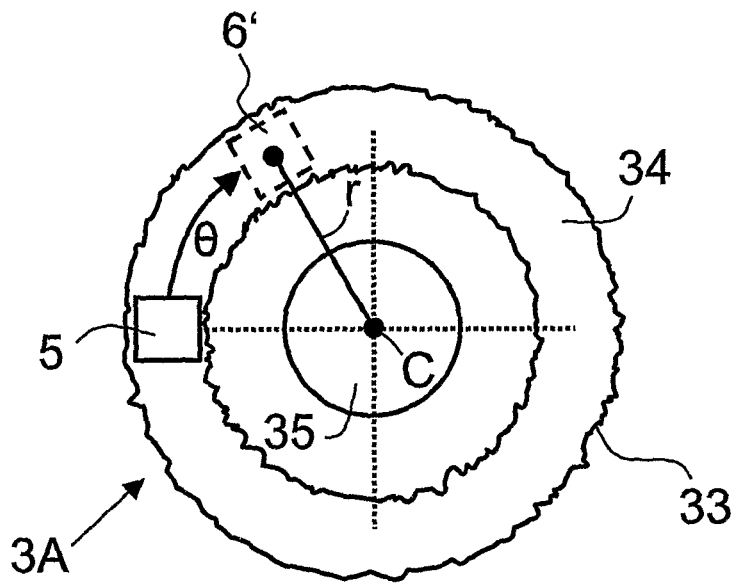
FIG. 7 illustrates schematically extraction of reference and comparative sections from the iris structure of an eye.

In step S4, the extraction module 132 extracts a set of at least one reference sections from the top view image 3A captured and stored in step S3. Preferably, the reference sections are extracted from the iris 34; particularly, from an area of the iris structure 34 that is essentially irremovable relative to the eye's eyeball; for example, an area that is essentially adjacent to the eye's limbus 33, e.g. an area adjacent to the eye's limbus 33 having a width of 1 to 2 mm. In FIG. 7, an example of the location of a reference section 5 in the top view image 3A is illustrated. In the example, the reference section 5 is located at a distance r of the rotation center C of the motion driver 15 (e.g. the rotation center C is the intersection of the optic axis Z with the surface of the eye 3).

For example, the reference section 5 is a pixel array having an equal number of rows and columns w×w (e.g. w=64). One skilled in the art will understand that different shapes and/or sizes of reference sections are possible. In alternative embodiments, the reference sections are extracted from vein patterns in the sclera 37 or from the edge of the pupil 38 (the latter is possible, for example, if the pupil is expanded through medication).

In step S5, the control module 131 makes the motion driver 15 move the opthalmological device 1 to the next (advanced) instrument position, e.g. the light projector 11 and the image-capturing means coupled with the motion driver 15 are rotated by a defined angle or transferred by a defined vector.

In step S6, the control module 131 makes the image-capturing means capture one or two cross-sectional images 30A, 30B as well as a top view image 3A from the new instrument position set in step S5. The cross-sectional images 30A, 30B and the top view image 3A from the current instrument position are stored assigned to each other.

In step S7, the extraction module 132 extracts a set of at least one comparative section from the top view image 3A captured and stored in step S6. In the embodiment where the image-capturing means for capturing the top view image are static (not coupled to the motion driver 15), the comparative sections are extracted from the top view image 3A in the same location as the reference section 5 (step S4). However, in the preferred embodiment where the image-capturing means for capturing the top view image are coupled to the motion driver 15, the comparative sections are extracted from the top view image 3A using a reverse transformation to compensate for movement of the image-capturing means. For example, when the current instrument position, and thus the location of a comparative section 6', is rotated by an angle θ from the initial instrument position, as illustrated in FIG. 7, the comparative section is extracted from the top view image 3A at a location rotated backwards by the same angle θ. This backwards rotation is achieved by the compensator module 133 applying a reverse transformation as described below.

The position [u, v] of the original pixels in the top view image 3A are given in the coordinate system of the image-capturing means for capturing top view images (e.g. the image-capturing device 12B or the image converter 120). The position [s, t] describes the pixels in the reference section 5 of size w×w. The rotation center C=[$u_c$, $v_c$] is determined during the calibration process of the opthalmological device 1. The position of the center of the reference section 5 of size w×w is assumed to be at the position [$x_0$, $y_0$], e.g. [−r, 0] in the example of FIG. 7. The position [s, t] of a comparative section 6, to be extracted from a top view image 3A taken after rotation θ, can be transformed by the compensator module 133 into the coordinates [u, v] in the top view image 3A as:

$$\begin{bmatrix} u \\ v \end{bmatrix} = \begin{bmatrix} \cos\theta & \sin\theta \\ -\sin\theta & \cos\theta \end{bmatrix} \begin{bmatrix} s - w/2 + x_0 \\ t - w/2 + y_0 \end{bmatrix} + \begin{bmatrix} u_c \\ v_c \end{bmatrix}$$

The resulting coordinates u and v are non-integer numbers that do not fit to the pixel raster of the top view image 3A. However, the intensity of the pixels of the reference section is obtained through a bicubic interpolation scheme using the neighboring pixels. Alternatively, a B-spline interpolation is used as proposed, for instance, by Unser, Splines, "A Perfect Fit for Signal and Image Processing", IEEE Signal Processing Magazine, vol. 16, no. 6, pp. 22-38, November 1999. It should be noted that the rotation angle θ is preferably provided by the motion driver 15; nevertheless, θ can also be determined from relative rotation of extracted sections. One skilled in the art will understand, that, correspondingly, a different reverse transformation can be used when the motion driver 15 provides for translatory movement rather than rotary movement.

In step S8, the measurement module 134 determines the displacement between the reference section 5, extracted in step S4, and the comparative section, extracted in step S7. The displacement is stored assigned to the cross-sectional images 30A, 30B captured in step S6. Preferably, phase correlation, used to measure translation between two patterns (of the reference and comparative sections), is used to determine the displacement. Given two w×w patterns f(x, y) and g(x, y), their 2D discrete Fourier transforms (2D DFTs) F($k_x$, $k_y$) and G($k_x$, $k_y$) are given by:

$$F(k_x, k_y) = \sum_{x,y} f(x, y) W_S^{k_x x} W_S^{k_y y} = A_F(k_x, k_y) e^{j\theta_F(k_x, k_y)} \quad (1)$$

$$G(k_x, k_y) = \sum_{x,y} g(x, y) W_S^{k_x x} W_S^{k_y y} = A_G(k_x, k_y) e^{j\theta_G(k_x, k_y)} \quad (2)$$

where w=2S+1, and $k_x$=−S . . . S, $k_y$=−S . . . S, and $$W_S = e^{-j\frac{2\pi}{S}}.$$

$A_F(k_x, k_y)$ and $A_G(k_x, k_y)$ are amplitude components and $e^{j\theta_F(k_x, k_y)}$ and $e^{j\theta_G(k_x, k_y)}$ are phase components. The cross spectrum R($k_x$, $k_y$) between F($k_x$, $k_y$) and G($k_x$, $k_y$) is defined as:

$$R(k_x, k_y) = F(k_x, k_y) G^*(k_x, k_y) = A_F(k_x, k_y) A_G(k_x, k_y) e^{j\theta(k_x, k_y)} \quad (3)$$

where $e^{j\theta(k_x, k_y)} = e^{j\theta_G(k_x, k_y)}$, and G*($k_x$, $k_y$) denotes the conjugate complex of G($k_x$, $k_y$). The cross-phase spectrum (or normalized spectrum) $\hat{R}(k_x, k_y)$ is defined as:

$$\hat{R} = \frac{F(k_x, k_y) G^*(k_x, k_y)}{|F(k_x, k_y) G(k_x, k_y)|} = e^{j\theta(k_x, k_y)} \quad (4)$$

The phase-correlation function r̂(x,y) is the 2D inverse discrete Fourier transform (2D IDFT) of $\hat{R}(k_x, k_y)$:

$$\hat{r}(x, y) = \frac{1}{S \cdot S} \sum_{k_x, k_y} \hat{R}(k_x, k_y) W_S^{-k_x x} W_S^{-k_y y} \quad (5)$$

If the two patterns $$g(x,y) = e(s,t) \quad (6)$$

and $$g(x,y) = e(s+\delta_x, t+\delta_y) \quad (7)$$

are spatially sampled patterns of the same larger pattern e(s,t) at different positions, where $\delta_x$ and δy are the displacements in x and y directions, respectively, and T is the spatial sampling interval, then the phase correlation function becomes:

$$\hat{r}(x,y) = \delta(x+\delta_x, y+\delta_y) \quad (8)$$

$\delta(x+\delta_x, y+\delta_y)$ is the Kronecker delta function, which is one only at the position ($\delta_x, \delta_y$) and zero elsewhere. Therefore, the translation between two patterns can easily be measured by determining the position ($\delta_x, \delta_y$) of the Kronecker delta in the phase-correlation function.

In a preferred embodiment, determination of the displacement is extended to sub-pixel displacement measurement. In the present application, for typical patterns of extracted sections, most of the energy is concentrated typically in the low spatial frequency components. Therefore, a low-pass-type weighting function H($k_x, k_y$) is applied to the cross-phase spectrum $\hat{R}(k_x, k_y)$. In order to get a well-defined peak in the phase-correlation function, a Gaussian weighting is used:

$$H(k_x, k_y) = e^{-2\pi^2 \sigma^2 (k_x^2 + k_y^2)} \quad (9)$$

where σ is a parameter that controls the function width. The phase-correlation function then becomes:

$$\hat{r}(x, y) = \frac{1}{S \cdot S} \sum_{k_x, k_y} \hat{R}(k_x, k_y) H(k_x, k_y) W_S^{-k_x x} W_S^{-k_y y} \quad (10)$$

which convolves the Kronecker delta function $\delta(x+\delta_x, y+\delta_y)$ with a Gaussian, resulting in:

$$\hat{r}_H(x, y) \cong \frac{1}{2\pi\sigma} e^{\frac{(x-\delta_x)^2 + (x-\delta_x)^2}{2\sigma^2}} \quad (11)$$

which is again a Gaussian. In order to find the translated position $(\delta_x, \delta_y)$ of this Gaussian peak with sub-pixel accuracy, a simplified model of the Gaussian is fitted to the phase-correlation result. The model is:

$$z(x,y) \cong a \cdot e^{-[b(x-\delta_x)^2 + c(x-\delta_x)^2]} - d \quad (12)$$

where a, b, c, d, $\delta_x$, and $\delta_y$ are the unknown model parameters. Rearranging Equation (12), and, for simplicity, writing only z instead of z(x, y), we obtain:

$$\log(z-d) = \log(a) - b(x^2 - 2\delta_x x + \delta_x^2) - c(y^2 - 2\delta_y y + \delta_y^2) \quad (13)$$

From this equation, the following linear system can be derived:

$$[x_i^2 \; x_i \; y_i^2 \; y_i \; 1] \cdot \begin{bmatrix} -b \\ -2b\delta_x \\ -c \\ -2c\delta_y \\ \log(a) - b\delta_x^2 - c\delta_y^2 \end{bmatrix} = \log(z_i - d) \quad (14)$$

This equation is abbreviated to:

AC=Z  (13)

and is solved as:

$$C = (A^T A)^{-1} Z \quad (15)$$

From the first four elements of C, the sub-pixel translation $(\delta_x, \delta_y)$ can easily be determined. Since the phase correlation function has a very sharp peak, a limited number of data points (e.g. m×m=3×3 . . . 9×9) around the maximum peak of $\hat{r}_H(x,y)$ are enough to achieve a high-accuracy least squares function fitting.

Figure 8:
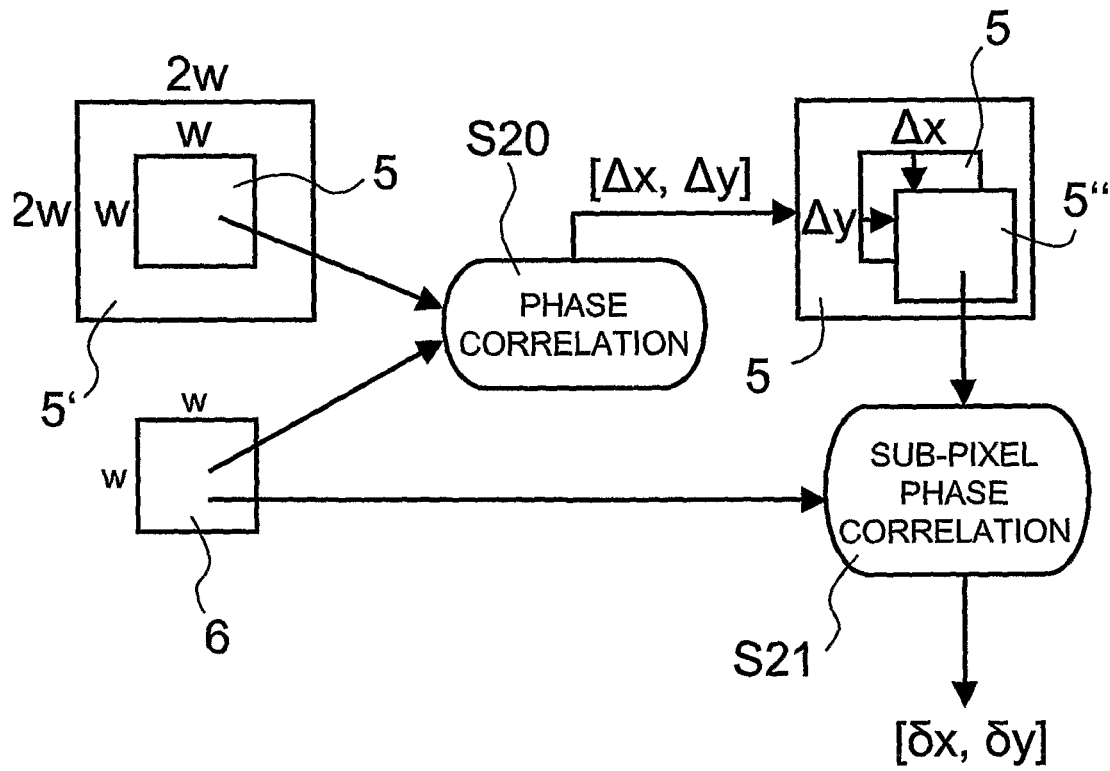
FIG. 8 shows a flow diagram of a possible sequence of steps for determining the displacement between the reference section and the comparative section.

The sub-pixel registration works best, when the displacement $[\delta_x, \delta_y]$ is small enough in comparison with the total image size w. This can be achieved, if a two-step coarse-to-fine approach is implemented, as illustrated in FIG. 8. The reference section 5' is extracted with a size larger than the partial section 5 used for phase-correlation, e.g. two times the size (2w×2w) of comparative sections (w×w). In a first step S20, a w×w partial section 5, placed in a defined location in the reference section 5', is processed with a comparative section 6 (associated with an advanced instrument position) by phase correlation. However, the sub-pixel registration using the fit to a Gaussian surface is omitted, and only the position $[\Delta_x, \delta_y]$ of the pixel with the maximum value is used in order to get a first shift only with pixel accuracy. The defined location is, for example, the center of the reference section 5'. Alternatively, the defined location is determined from previous displacement measures, estimating an expected location of the comparative section. In a second step S21, a new partial section 5'' is extracted from the reference section 5', which is shifted by $[\Delta_x, \Delta_y]$ from the center. Using this new partial section 5'', and processing it with comparative section 6 (associated with the advanced instrument position) by applying sub-pixel registration, the sub-pixel shift $[\delta_x, \delta_y]$ is computed. The total shift is then $[\Delta_x + \delta_x, \Delta_y + \delta_y]$, which is the displacement value resulting from the present iris pattern motion detection process.

In an embodiment, the measurement module 134 is further configured to determine in step S8 cyclotorsion or cyclorotation of the eye 3. Cyclotorsion or cyclorotation of the eye 3 is preferably determined from a set of multiple reference sections extracted in step S4 and from a set of multiple comparative sections extracted in step S7. For example, cyclotorsion or cyclorotation of the eye 3 is determined from the displacement between a first pair of corresponding reference and comparative sections and from the displacement between a second pair of corresponding reference and comparative sections. Alternatively, cyclotorsion or cyclorotation of the eye 3 is determined from the displacement between the reference section and the comparative section, and from a displacement determined between reflections in the initial top view image 3A, captured in step S3, and reflections in the top view image 3A, captured in step S6 at the current (advanced) instrument position.

In step S9, the control module 131 checks whether a full measurement cycle with all defined instruments positions has been processed (e.g. full rotation back to initial instrument position). If there are further instrument positions to be processed, the control module 131 continues in step S5 and moves the opthalmological device 1 to next instrument position. Otherwise, if all instrument positions have been processed, the control module 131 continues in step S10.

In step S10, the positioning module 135 positions the cross-sectional image(s) 30A, 30B, captured in step S6 relative to the cross-sectional image(s) 30A, 30B, captured in step S3, based on the displacement, determined in step S8. In essence the displacement is a measure for the movement of the eye relative to the opthalmological device 1. The displacement determined from top view images 3A is transformed into a translational and rotational displacement in three dimensional space based on geometrical parameters of the calibrated opthalmological device 1. Thus, based on the knowledge of the respective instrument position and based on the (eye) displacement, the positioning module 135 positions relative to each other the cross-sectional image(s) 30A, 30B captured during an entire measurement cycle. The iris pattern motion detection and cross-sectional image alignment process ends in step S11.

One skilled in the art will understand that different sequences of steps S1-S11 are possible without deviating from the scope of the present invention. For example, step S7, or steps S7 and S8, can be processed after step S9, when all imaging data has been captured, e.g. after a full measurement cycle.

Using the composition module 136, the plurality of cross-sectional images 30A, captured, stored, and positioned relative to one another are merged to a three-dimensional image of the anterior chamber structures of the eye 3, in particular of the cornea 30.

The measurement module 134 is further configured to determine eye structures in the captured and stored cross-sectional images 30A, 30B, in particular images of the cornea with the anterior corneal surface 31A, 31B and the posterior corneal surface 32A, 32B, and to determine distances, or respectively thicknesses, based thereon, in particular the measurement values $D_A$ and $D_B$ of the distances between the anterior corneal surface 31A, 31B and the posterior corneal surface 32A, 32B for determination of the corneal thickness D.

The electrical supply of the opthalmologic device 1 takes place through an internal energy source or through an external energy source connected by means of cable.

The opthalmological device 1 also comprises a display 14 on which determined measurement values and/or application aids are shown.

What is claimed is:

1. An ophthalmological device, comprising:
a light projector configured to project a beam of rays through a cross-sectional portion of an eye;
first image-capturing means disposed in Scheimpflug configuration with respect to the beam of rays and configured to capture in a first instrument position a cross-sectional image of at least a sub-area of the cross-sectional portion, illuminated by the light projector;
a motion driver configured to move the first image-capturing means to a second instrument position, at which second instrument position the first image-capturing means are disposed in Scheimpflug configuration with respect to the beam of rays;
second image-capturing means configured to capture a first top view image of at least part of the eye, while capturing the cross-sectional image in the first instrument position, and a second top view image of at least part of the eye, while capturing the cross-sectional image in the second instrument position, the second image-capturing means being linked to and moved by the motion driver;
an extraction module configured to extract at least one reference section from the first top view image, and to extract at least one comparative section from the second top view image in a location obtained through a reverse transformation to compensate for movement of the second image-capturing means by the motion driver;
a measurement module configured to determine a displacement between the reference section extracted from the first top view image and the comparative section extracted from the second top view image; and
a positioning module configured to position relative to each other cross-sectional images, captured in the first instrument position and the second instrument position, based on the displacement determined between the reference section extracted from the first top view image and the comparative section extracted from the second top view image.

2. The device of claim 1, wherein the extraction module is configured to extract the at least one reference section from an iris structure in the first top view image, and to extract the at least one comparative section from the iris structure in the second top view image.

3. The device of claim 2, wherein the extraction module is configured to extract the reference and comparative sections from an iris structure that is essentially irremovable relative to the eye's eyeball.

4. The device of claim 2, wherein the extraction module is configured to extract the reference and comparative sections from an iris structure that is essentially adjacent to the eye's limbus.

5. The device of claim 1, wherein the measurement module is further configured to determine cyclotorsion and/or cyclorotation of the eye from a combination of a first set of sections, comprising at least a first reference section and a corresponding first comparative section, and a second set of sections, comprising at least a second reference section and a corresponding second comparative section.

6. The device of claim 1, wherein the second image-capturing means are further configured to capture with the first and second top view images reflections on the eye;
and wherein the measurement module is further configured to determine cyclotorsion and/or cyclorotation of the eye from the displacement between the reference section and the comparative section, and from a displacement determined between reflections in the first top view image and reflections in the second top view image.

7. The device of claim 1, wherein the second image-capturing means are coupled with the motion driver such that the first top view image is captured from a position linked with the first instrument position, and the second top view image is captured from a position linked with the second instrument position; and wherein the device further comprises a compensator module configured to determine the at least one comparative section from the second top view image, using a reverse transformation to compensate for movement of the second image-capturing means.

8. The device of claim 1, wherein the measurement module is configured to determine the displacement using a phase-correlation algorithm.

9. The device of claim 8, wherein the measurement module is configured to determine the displacement using sub-pixel phase-correlation.

10. The device of claim 1, wherein the extraction module is configured to extract the reference section with an area larger than the area of the comparative section; wherein the measurement module is configured to determine an initial displacement value using a phase-correlation algorithm for the comparative section and a partial reference section having a defined location within the reference section; and wherein the measurement module is configured to determine the displacement using sub-pixel phase-correlation for the partial reference section being moved off the defined location by the initial displacement value.

11. The device of claim 10, wherein the measurement module is configured to determine the defined location of the partial reference section from one of previous displacement measures and the center of the reference section.

12. The device of claim 1, wherein the motion driver is configured to rotate the light projector and the first image-capturing means essentially about a normal to the surface of the eye, turned toward the light projector, or to shift them substantially perpendicular to this normal.

13. The device of claim 1, wherein the extraction module is configured to extract the reference and comparative sections as an array having equal number of rows and columns.

14. An ophthalmological measuring method, comprising:
projecting a beam of rays through a cross-sectional portion of an eye;
capturing in a first instrument position a cross-sectional image of at least a sub-area of the cross-sectional portion, illuminated by the light projector, by first image-capturing means disposed in Scheimpflug configuration with respect to the beam of rays;
moving the first image-capturing means to a second instrument position, at which second instrument position the first image-capturing means are disposed in Scheimpflug configuration with respect to the beam of rays;
capturing, by second image-capturing means which are moved together with the first image-capturing means, a first top view image of at least part of the eye, while capturing the cross-sectional image in the first instrument position, and a second top view image of at least part of the eye, while capturing the cross-sectional image in the second instrument position;

extracting at least one reference section from the first top view image, and extracting at least one comparative section from the second top view image in a location obtained through reverse transformation to compensate for movement of the second image-capturing means;

determining a displacement between the reference section extracted from the first top view image and the comparative section extracted from the second top view image; and positioning relative to each other cross-sectional image, captured in the first instrument position and the second instrument position, based on the displacement determined between the reference section extracted from the first top view image and the comparative section extracted from the second top view image.

15. The method of claim 14, wherein the at least one reference section is extracted from an iris structure in the first top view image; and wherein the at least one comparative section is extracted from the iris structure in the second top view image.

16. The method of claim 15, wherein the reference and comparative sections are extracted from an iris structure that is essentially irremovable relative to the eye's eyeball.

17. The method of claim 15, wherein the reference and comparative sections are extracted from an iris structure that is essentially adjacent to the eye's limbus.

18. The method of claim 14, further comprising determining cyclotorsion and/or cyclorotation of the eye from a combination of a first set of sections, comprising at least a first reference section and a corresponding first comparative section, and a second set of sections, comprising at least a second reference section and a corresponding second comparative section.

19. The method of claim 14, further comprising capturing reflections on the eye with the first and second top view image; determining a reflection displacement between reflections in the first top view image and reflections in the second top view image; and
determining cyclotorsion and/or cyclorotation of the eye from the displacement, between the reference section and the comparative section, and from the reflection displacement.

20. The method of claim 14, further comprising moving the second image-capturing means together with the first image-capturing means, such that the first top view image is captured from a position linked with the first instrument position, and the second top view image is captured from a position linked with the second instrument position; and
determining the at least one comparative section from the second top view image, using a reverse transformation to compensate for movement of the second image-capturing means.

21. The method of claim 14, wherein the displacement is determined using a phase-correlation algorithm.

22. The method of claim 21, wherein the displacement is determined using sub-pixel phase-correlation.

23. The method of claim 14, wherein the reference section is extracted with an area larger than the area of the comparative section; wherein an initial displacement value is determined using a phase-correlation algorithm for the comparative section and a partial reference section having a defined location within the reference section; and wherein the displacement is determined using sub-pixel phase-correlation for the partial reference section being moved off the defined location by the initial displacement value.

24. The method of claim 23, wherein the defined location of the partial reference section is determined from one of previous displacement measures and the center of the reference section.

25. The method of claim 14, wherein the light projector and the first image-capturing means are rotated essentially about a normal to the surface of the eye turned towards the light projector, or shifted substantially perpendicular to this normal.

26. The method of claim 14, wherein the reference and comparative sections are extracted as an array having equal number of rows and columns.

27. An ophthalmological device, comprising:
a light projector configured to project a beam of rays through a cross-sectional portion of an eye;
first image-capturing means disposed in Scheimpflug configuration with respect to the beam of rays and configured to capture in a first instrument position a cross-sectional image of at least a sub-area of the cross-sectional portion, illuminated by the light projector;
a motion driver configured to move the first image-capturing means to a second instrument position, at which second instrument position the first image-capturing means are disposed in Scheimpflug configuration with respect to the beam of rays;
second image-capturing means configured to capture a first top view image of at least part of the eye, while capturing the cross-sectional image in the first instrument position, and a second top view image of at least part of the eye, while capturing the cross-sectional image in the second instrument position, the second image-capturing means being fixed and not moved by the motion driver;
an extraction module configured to extract at least one reference section as a part from the first top view image, and to extract at least one comparative section, in the same location as the reference section, as a part from the second top view image;
a measurement module configured to determine a displacement between the reference section extracted from the first top view image and the comparative section extracted in the same location as the reference section from the second top view image; and
a positioning module configured to position relative to each other cross-sectional images, captured in the first instrument position and the second instrument position, based on the displacement determined between the reference section extracted from the first top view image and the comparative section extracted in the same location as the reference section from the second top view image.

28. An ophthalmological measuring method, comprising:
projecting a beam of rays through a cross-sectional portion of an eye;
capturing in a first instrument position a cross-sectional image of at least a sub-area of the cross-sectional portion, illuminated by the beam of rays, by first image-capturing means disposed in Scheimpflug configuration with respect to the beam of rays;
moving the first image-capturing means to a second instrument position, at which second instrument position the first image-capturing means are disposed in Scheimpflug configuration with respect to the beam of rays;
capturing, by second image-capturing means which are static, a first top view image of at least part of the eye, while capturing the cross-sectional image in the first instrument position, and a second top view image of at least part of the eye, while capturing the cross-sectional image in the second instrument position;

extracting at least one reference section as a part from the first top view image, and extracting at least one comparative section, in the same location as the reference section, as a part from the second top view image;

determining a displacement between the reference section extracted from the first top view image and the comparative section extracted in the same location as the reference section from the second top view image; and positioning relative to each other cross-sectional image, captured in the first instrument position and the second instrument position, based on the displacement determined between the reference section extracted from the first top view image and the comparative section extracted in the same location as the reference section from the second top view image.

* * * * *